US012683015B2

(12) United States Patent
Schmuecking et al.

(10) Patent No.: US 12,683,015 B2
(45) Date of Patent: Jul. 14, 2026

(54) TECHNIQUE FOR MULTI-MODALITY MEDICAL IMAGE CLINICAL WORKFLOW GUIDANCE

(71) Applicant: Siemens Healthineers AG, Forchheim (DE)

(72) Inventors: Ingo Schmuecking, Yardley, PA (US); Puneet Sharma, Princeton Junction, NJ (US)

(73) Assignee: Siemens Healthineers AG, Forchheim (DE)

( * ) Notice: Subject to any disclaimer, the term of this patent is extended or adjusted under 35 U.S.C. 154(b) by 79 days.

(21) Appl. No.: 18/781,065

(22) Filed: Jul. 23, 2024

(65) Prior Publication Data

US 2025/0054609 A1    Feb. 13, 2025

(30) Foreign Application Priority Data

Aug. 10, 2023    (EP) ..................................... 23190885

(51) Int. Cl.
| | |
|---|---|
| *G16H 30/40* | (2018.01) |
| *G06F 40/40* | (2020.01) |
| *G06V 10/774* | (2022.01) |
| *G06V 10/94* | (2022.01) |
| *G06V 20/50* | (2022.01) |
| *G06V 20/70* | (2022.01) |

(Continued)

(52) U.S. Cl.
CPC ............. *G16H 30/40* (2018.01); *G06F 40/40* (2020.01); *G06V 10/774* (2022.01); *G06V 10/945* (2022.01); *G06V 20/50* (2022.01);

*G06V 20/70* (2022.01); *A61B 6/5247* (2013.01); *A61B 8/5261* (2013.01); *G06V 2201/03* (2022.01)

(58) Field of Classification Search
None
See application file for complete search history.

(56) References Cited

U.S. PATENT DOCUMENTS

| | | | |
|---|---|---|---|
| 2008/0055239 A1 * | 3/2008 | Garibaldi .............. | G06F 3/0481 |
| | | | 345/156 |
| 2009/0150184 A1 * | 6/2009 | Spahn .................... | G16H 30/20 |
| | | | 705/2 |

(Continued)

OTHER PUBLICATIONS

Lang Roberto, M., et al. "Recommendations for cardiac chamber quantification by echocardiography in adults: an update from the American Society of Echocardiography and the European Association of Cardiovascular Imaging." Journal of the American Society of Echocardiography 28.1 (2015): 1-39.

(Continued)

*Primary Examiner* — John A Pauls

(57) ABSTRACT

A computer-implemented method for multi-modality medical image clinical workflow guidance comprises a step of receiving a user input (306-4) in relation to a first medical image data set (306-2) acquired by means of a first medical imaging modality (304-A). By means of a clinical-concept-to-medical-image linking algorithm (314), the received user input (306-4) is assessed in view of at least one second medical image data set (308-1) acquired by means of at least one second medical imaging modality (304-B). An indication of a clinical workflow guidance in relation to the at least one second medical image data set (308-1) is output.

14 Claims, 6 Drawing Sheets

(51) Int. Cl.
*A61B 6/00* (2006.01)
*A61B 8/00* (2006.01)

(56) References Cited

U.S. PATENT DOCUMENTS

| | | | |
|---|---|---|---|
| 2018/0137244 A1 | 5/2018 | Sorenson | |
| 2018/0308580 A1* | 10/2018 | Mankovich | G16H 30/20 |
| 2019/0205792 A1* | 7/2019 | Huang | G06F 9/4881 |
| 2022/0354466 A1* | 11/2022 | Gomes | G06T 7/11 |
| 2022/0414883 A1 | 12/2022 | Shinagawa | |
| 2023/0334655 A1 | 10/2023 | Schmuecking | |
| 2024/0311580 A1* | 9/2024 | Achara | G06F 16/383 |

OTHER PUBLICATIONS

Mitchell, Carol, et al. "Guidelines for performing a comprehensive transthoracic echocardiographic examination in adults: recommendations from the American Society of Echocardiography." Journal of the American Society of Echocardiography 32.1 (2019): 1-64.
Zhang, Jingyi, et al. "Vision-language models for vision tasks: A survey." IEEE Transactions on Pattern Analysis and Machine Intelligence (2024). pp. 1-24.
Extended European Search Report (EESR) mailed Feb. 7, 2024 in corresponding European Patent Application No. 23190885.6.

* cited by examiner

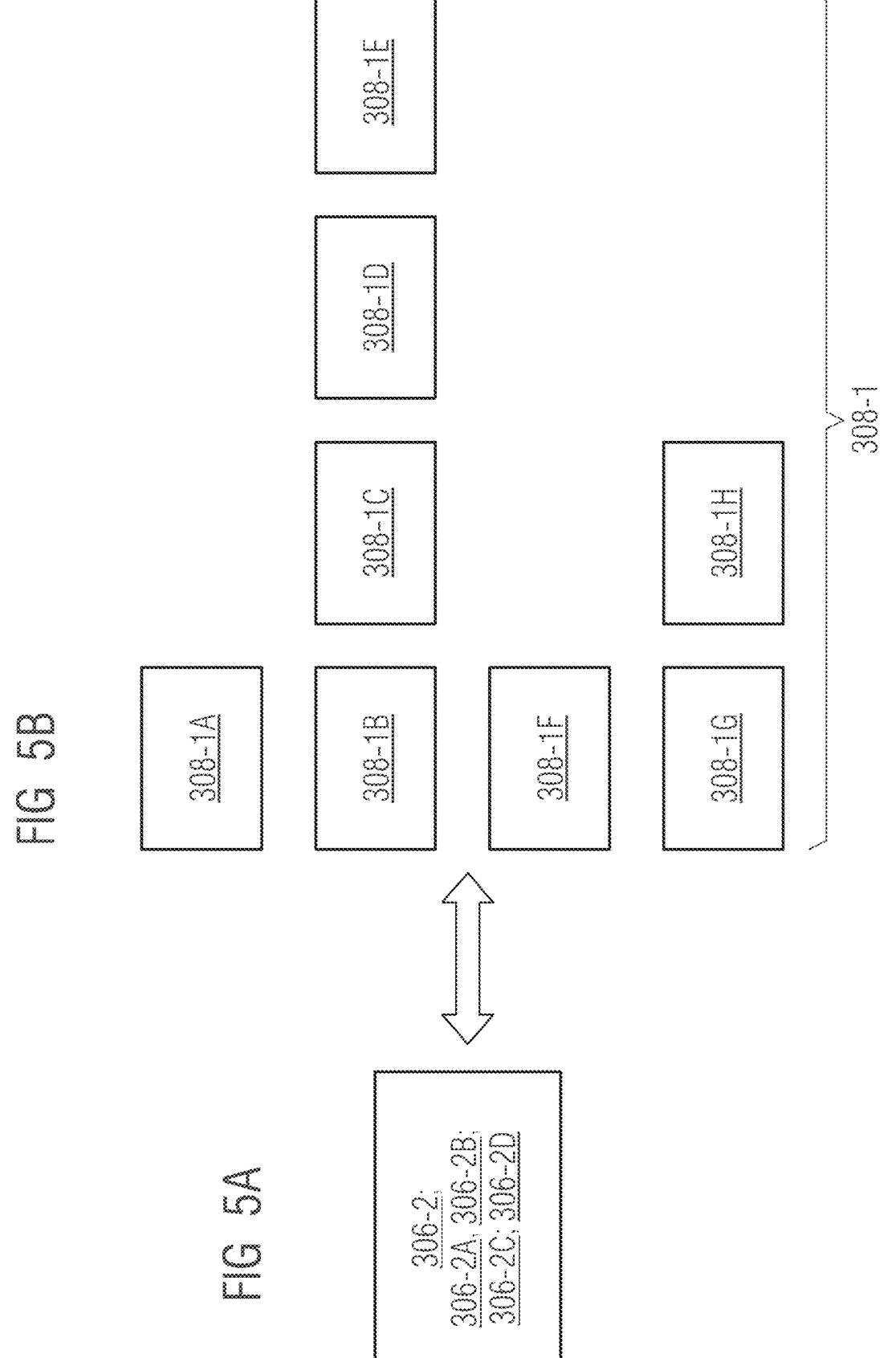

TECHNIQUE FOR MULTI-MODALITY MEDICAL IMAGE CLINICAL WORKFLOW GUIDANCE

The present invention relates to a technique for multi-modality medical image clinical workflow guidance, in particular comprising a method, a computing device, a system comprising the computing device, and a computer program product.

Multi-modality medical imaging is at the core of cardio-vascular, medicine from diagnosis to therapy and follow-up providing complementary information on cardiovascular, anatomy and function.

A cardiovascular imaging and information system (CVIS) increasingly supports medical images from multiple cardio-vascular medical imaging modalities which can be stored, opened and displayed in the same application. However, working with multi-modality medical images is convention-ally challenging due to the large number of medical images and the complexity of cardiovascular anatomy and function. For example, echocardiography studies may have 100+ images and/or clips containing different views of the cardiac anatomy and function. Comparing images across medical imaging modalities conventionally requires time-consuming manual steps, such as querying the studies to search for the right medical images, arranging them in the viewport and aligning them spatially and temporally. Conventionally, cli-nicians may have to perform many manual steps until the actual image interpretation task can begin.

In many situations, clinicians have to use different image review products to access images from multiple cardiovas-cular modalities. Even if the images are in the same appli-cation, the clinicians conventionally need to spend valuable time and energy to search images and manually arrange them in a meaningful way for comparison. This may con-ventionally need to be repeated many times in order to capture different views of the cardiac anatomy. When align-ment of images or views requires too much time, clinicians conventionally tend to use their image review skills to compensate for the differences.

The use cases in a CVIS require a conventionally lacking broad support for multi-modality image querying and work-flow guidance as the specific need depends on the case that is being reviewed and the imaging data available for this case.

It is therefore an object of the present invention to provide a solution for improved multi-modality medical image clini-cal workflow guidance, in particular in terms of time and/or energy efficiency, and/or in terms of accuracy.

This object is solved by a (in particular computer-imple-mented) method for multi-modality medical image clinical workflow guidance, by a computing device, by a system comprising the computing device, by a computer program (and/or computer program product), and by a computer-readable medium according to the appended independent claims. Advantageous aspects, features and embodiments are described in the dependent claims and in the following description together with advantages.

In the following the solution according to the invention is described with respect to the claimed computer-imple-mented method for multi-modality medical image clinical workflow guidance as well as with respect to the claimed computing device. Features, advantages or alternative embodiments herein can be assigned to the other claimed objects (e.g., the system, the computer program or a com-puter program product), and vice versa. In other words, claims for the computing device, and/or the system comprising the computing device, can be improved with features described or claimed in the context of the method. In this case, the functional features of the method are embodied by structural units of the computing device (and/or system) and vice versa, respectively.

As to a method aspect, a (in particular computer-imple-mented) method for multi-modality medical image clinical workflow guidance is provided. The method comprises a step of receiving a user input in relation to a first medical image data set acquired by means of a first medical imaging modality. The method further comprises a step of assessing, by means of a clinical-concept-to-medical-image linking algorithm, the received user input in view of at least one second medical image data set acquired by means of at least one second medical imaging modality. The method further comprises a step of outputting an indication of a clinical workflow guidance in relation to the at least one second medical image data set.

By the inventive technique, a clinical workflow, and/or a result of the clinical workflow, may be improved, e.g., in terms of time and accuracy. In particular, a diagnosis and/or severity assessment of a medical condition, in particular a cardiac condition, may be improved, e.g., in terms of time and accuracy. Alternatively or in addition, by the inventive technique, procedure planning measures (and/or measure-ments) and/or post-surgical (and/or post-procedure) control measures (and/or measurements) may be improved, in par-ticular in terms of time and accuracy. E.g., multiple mea-surements based on multiple medical images from multiple medical imaging modalities, in particular from cardiac examinations, may be performed in a timely manner, and/or the multiple medical images may be aligned spatially and/or temporally. Alternatively or in addition, by the clinical-concept-to-medical-image linking algorithm, the at least one second medical image data set may be selected for the best quality of the available data, and/or in view of the clinical question (and/or clinical context), in particular in view of assessing a cardiac function of a patient.

Any one of the medical imaging modalities (in particular the first and/or the at least one second medical imaging modality) may comprise computed tomography (CT), ultra-sound (US), magnetic resonance tomography (MRT), X-ray imaging (also denoted as radiography), and/or catheteriza-tion (cath). Alternatively or in addition, any one of the medical imaging modalities may comprise electrocardiog-raphy (ECG).

Any one of the medical image data sets (in particular the first and/or the at least one second medical image data set) may comprise a waveform image data set (e.g., acquired by means of ECG).

According to an embodiment, the at least one second medical imaging modality may be identical to (and/or may be the same as) the first medical imaging modality. E.g., the at least one second medical image data set may comprise a follow-up medical image acquired with the same medical imaging modality.

According to another embodiment, the first medical imag-ing modality may differ from the at least one second medical imaging modality. E.g., the first imaging modality may comprise CT, and the at least one second imaging modality may comprise transthoracic echocardiography (TTE).

The multi-modality may comprise two or more different medical imaging modalities. Alternatively or in addition, the inventive technique may be applied to three or more medical imaging modalities. E.g., echocardiography (also denoted as ultrasound of the heart, and/or abbreviated as "echo") may be combined with MRT and CT. Alternatively or in addition, echo may be combined with MRT and cath. Further alternatively or in addition, current echo, prior each and MRT may be combined.

Alternatively or in addition, by the inventive technique, current and prior medical images from the same medical imaging modality may be combined, e.g., for performing an efficient and precise prior comparison with clinical context focusing on relevant aspects.

Any one of the medical imaging modalities (in particular the first and/or the at least one second medical imaging modality) may be configured for cardiac (and/or cardiovascular) imaging. In particular, any one of the medical imaging modalities (in particular the first and/or the at least one second medical imaging modality) may comprise echocardiography (and more particularly TTE), cardiac MRT, and/or radionuclide myocardial perfusion imaging (MPI).

Any one of the medical image data sets acquired by any one of the medical imaging modalities may comprise image data in relation to a patient (e.g., the same patient across all medical imaging modalities).

The image data (also denoted as medical image), and/or the medical image data set, may be provided in the time domain, space domain, and/or frequency domain (e.g., in k-space for MRT, and/or as waveforms for ECG). Alternatively or in addition, the image data (also denoted as medical image), and/or the medical image data set, may comprise a temporal sequence (also denoted as cine sequence) of (in particular still) frames.

The first medical image data set may comprise (in particular textual) metadata indicative of the content of the comprised first medical image (and/or the first image data). Alternatively or in addition, the at least one second medical image data set may comprise (in particular textual) metadata indicative of the content of the comprised in the at least one second medical image.

Herein, the metadata of any medical image data set may extend (and/or may go beyond) the information conventionally comprised in a digital imaging and communications in medicine (DICOM) header. The extended information may comprise information on anatomical structures (e.g., a number and/or type of cardiac chambers) comprised in the medical image data set, information on anatomical views (e.g., long axis, LAX, or short axis, SAX), information on a zoom level, a cardiac phase, use of contrast enhancement, an image quality assessment, and/or a score tailored to use cases (e.g., based on a combination of the image quality assessment, cardiac phase, and/or anatomical structures comprised in the medical image data set).

The metadata may be provided in a structured format, e.g., in a table, spreadsheet, and/or as comma-separated values (CSV).

The first medical image data set, and/or the at least one second medical image data set may be stored locally (e.g., centrally at a clinical site), and/or in a cloud.

The user may be a medical practitioner, physician, clinician and/or radiologist (e.g., radiation oncologist).

The user input (also denoted as user interaction, and/or user feedback) may comprise selecting the first medical image data set. Alternatively or in addition, the user input may comprise selecting a (in particular two-dimensional, 2D) view of the (in particular three-dimensional, 3D) medical image data comprised in the first medical image data set. Further alternatively or in addition, the user input may comprise performing a measurement on (e.g., the 2D view of) the (e.g., 3D) medical image data, and/or marking a location on the medical image data (e.g., marking a region of interest, ROI, in particular based on movements of a cursor). Still further alternatively or in addition, the user input may comprise selecting a (e.g., still) frame from a temporal sequence (and/or cine sequence) of medical images comprised in the medical image data set.

The clinical-concept-to-medical-image linking algorithm may comprise one or more (e.g., interconnected, and/or jointly trained) artificial intelligence (AI) models.

Any (in particular AI) model may alternatively be denoted as network, and/or may comprise an algorithm.

The clinical-concept-to-medical-image linking algorithm may comprise a textual clinical concept algorithm (also denoted as large language model, LLM) and a semantic image understanding algorithm (which may alternatively be denoted as semantic image extraction algorithm, and/or as semantic image relationship algorithm, and/or abbreviated as SIU). Any algorithm may alternatively be denoted as model.

The textual clinical concept algorithm (and/or the LLM) may be configured for processing, and/or may comprise, clinical concepts and/or clinical context information.

Alternatively or in addition, the semantic image understanding algorithm (and/or the SIU) may be configured for providing details on an image content of a medical image data set (in particular of the first medical image data set, and/or the at least one second medical image data set). The details may be provided in terms of metadata of the corresponding medical image data set.

The clinical-concept-to-medical-image linking algorithm may be configured for linking metadata of the first medical image data set (in particular provided by the semantic image understanding algorithm) to clinical concepts and/or clinical context information (in particular comprised in the textual clinical concept algorithm). The clinical concepts and/or clinical context information may then be used to assess metadata of the at least one second medical image data set.

The outputted indication (which may also be denoted as prompt) of the clinical workflow guidance may comprise a proposed (e.g., corresponding or complementary) anatomical view of the at least one second medical image data set, a complementary image indicative of a (in particular cardiac) function, and/or a recommendation for a next step in the clinical workflow.

The next step in the clinical workflow may comprise acquiring at least one further medical image data set, and/or performing measurements on the available (in particular first, and/or at least one second) medical image data sets.

Alternatively or in addition, the next step may comprise the display (e.g., on a screen) of one or more corresponding or complementary images (and/or anatomical views) together (e.g., side by side) for visual assessment by the user (e.g., the physician and/or medical practitioner). Alternatively or in addition, the next step may comprise an anatomy alignment of the medical images comprised in the first medical image dataset and the at least one second medical image dataset.

The display, and/or the anatomy alignment, may be performed without performing measurements. E.g., a cardiac function may be analysed both quantitatively (e.g., as ejection fraction, EF) and/or qualitatively (e.g., visually) by reviewing wall motion across all cardiac segments.

The first medical imaging modality may be different from the at least one second medical imaging modality.

The at least one second medical image data set (and/or the first medical image data set) may comprise a temporal sequence of medical image data acquired by means of the at least one second medical imaging modality (and/or by means of the first medical imaging modality). The temporal sequence of medical image data may also be denoted as cine data set. Alternatively or in addition, any medical image data set may briefly be denoted as image data set.

In one embodiment, the first medical image data set may comprise a cardiac CT image, and the at least one second medical image data set may comprise an echo series of images acquired using TTE.

The first medical image data set, and/or the at least one second medical image data set, may be aligned spatially (e.g., concerning the anatomy by providing a complementary or corresponding anatomical view) and/or temporally (e.g., concerning the time of examination).

E.g., three medical image data sets may be obtained by means of echo, MRT and CT. Alternatively or in addition, three medical image dataset may be obtained by means of echo, MRT and cath.

Alternatively or in addition, a subset (or all) of the medical imaging modalities may be identical.

E.g., three medical image data sets may comprise a current echo image data set, a prior echo image data set and an MRT image data set.

Any one of the medical image data sets (in particular the first medical image data set and/or the at least one second medical image data set=may comprises a 2D image data set. Alternatively or in addition, any one of the medical image data sets may comprise a 3D image data set.

The 2D image data set may also be denoted as planar image data set. E.g., any US image data set and/or echocardiography image data set may comprise a 2D image.

The 3D image data set may also be denoted as volumetric image data set. E.g., any CT image data set and/or MRT image data set may comprise volumetric data.

Any one of the medical imaging modalities (in particular the first medical imaging modality and/or the at least one second medical imaging modality) may comprise CT, in particular cardiac CT. Alternatively or in addition, any one of the medical imaging modalities (in particular the first medical imaging modality and/or the at least one second medical imaging modality) may comprise US, in particular vascular US and/or intravascular ultrasound (IVUS). Further alternatively or in addition, any one of the medical imaging modalities (in particular the first medical imaging modality and/or the at least one second medical imaging modality) may comprise echocardiography, in particular TTE, transesophageal echocardiography (TEE), and/or intracardiac echocardiography (ICE).

Further alternatively or in addition, any one of the medical imaging modalities (in particular the first medical imaging modality and/or the at least one second medical imaging modality) may comprise MRT, in particular cardiac MRT. Further alternatively or in addition, any one of the medical imaging modalities (in particular the first medical imaging modality and/or the at least one second medical imaging modality) may comprise radiography (also denoted as X-ray imaging). Further alternatively or in addition, any one of the medical imaging modalities (in particular the first medical imaging modality and/or the at least one second medical imaging modality) may comprise cath, and/or fractional flow reserve (FFR). Further alternatively or in addition, any one of the medical imaging modalities (in particular the first medical imaging modality and/or the at least one second medical imaging modality) may comprise optical coherence tomography (OCT) and/or nuclear cardiology imaging, in particular single-photon emission computed tomography (SPECT), positron emission tomography (PET) and/or radionuclide MPI.

Catheterization (cath) may comprise catheter angiography, and/or coronary angiography.

Radionuclide MPI may alternatively be abbreviated as Nuc Card.

The multi-modality medical imaging may comprise cardiac and/or cardiovascular imaging.

The clinical workflow guidance may be configured for analysing a cardiac (and/or cardiovascular) function in relation to a patient.

The clinical-concept-to-medical-image linking algorithm may comprise a textual clinical concept algorithm (and/or LLM) configured for processing clinical context information. Alternatively or in addition, the clinical-concept-to-medical-image linking algorithm may comprise a semantic image understanding algorithm (and/or SIU) configured for providing details on the image content of the first medical image data set and/or the at least one second medical image data set.

The semantic image understanding algorithm (and/or SIU) may generate metadata in relation to the first medical image data set, and/or in relation to the at least one second medical image data set. The metadata may be indicative of a view classification, one or more anatomical landmarks and/or anatomical structures, a zoom level, a cardiac phase identification, a contrast enhancement, an image quality assessment, and/or a score for use cases. Optionally, the score may be based on an image quality assessment at a predetermined phase within the cardiac cycle, and/or based on anatomical structures comprised in the corresponding medical image data set.

The view classification may comprise an apical four-chamber view (A4C), or any other main view or subtype thereof.

The anatomical landmark may comprise, e.g., a mitral valve, a (e.g., true) left ventricular (LV) apex, and/or a tricuspid valve.

The anatomical structure may comprise, e.g., the left ventricle (LV), right ventricle (RV), left atrium (LA), right atrium (RA), and/or mitral valve (MV).

The cardiac phase may comprise end diastole and/or end systole within a cardiac phase.

The contrast enhancement may, e.g., refer to a cardiac chamber such as the LV.

The image quality assessment may, e.g., comprise a noise level, signal-to-noise ratio (SNR), a signal-to-interference-and-noise ratio (SINR), contrast-to-noise ratio (CNR), image artifacts, and/or image quality of relevant anatomical structures.

Image quality may have an impact on the ability of users (e.g., clinicians) to interpret the medical images (and/or, in particular first and/or at least one second, medical image data set). Alternatively or in addition, image quality may impact the quality of artificial intelligence (AI) results (e.g., in view of segmentations and/or classifications).

E.g., an echo clip (and/or temporal sequence of frames, in particular covering the cardia cycle) may have noise and/or image artifacts only on some frames of the clip (in particular, not on all frames), which may impact the ability to use the clip (and/or in particular the frames affected by the noise and/or image artefacts) for interpretation.

The score for use cases may indicate a suitability of the medical image data set for performing a predetermined diagnosis, assessing a medical condition, performing a measurement, procedure planning, and/or post-surgical (and/or post-procedure) control (as examples of use cases).

The clinical-concept-to-medical-image linking algorithm may comprise at least one trained artificial intelligence (AI) model, in particular two jointly trained AI models.

AI models can be trained jointly on imaging and text data, e.g., by means of one or more vision-language processing approaches, as described, e.g., in arXiv: 2304.00685v1 [cs.CV] by Jingyi Zhang et al. [1], which is incorporated herein by reference.

According to an embodiment, two networks (and/or AI models) are connected by iterative and/or continuous cycles of queries and prompts.

According to a further embodiment, a further network and/or further model (e.g., denoted as AI-powered orchestrator) may be located in between (e.g., in terms of a data connection) the sematic image understanding algorithm (and/or SIU) and the textual clinical concept algorithm (and/or LLM).

E.g., the semantic image understanding algorithm (and/or SIU) for a cardiovascular imaging study (e.g., comprising echo with 100+ images and/or clips) may provide a large amount of information, which may be more than what the textual clinical concept algorithm (and/or LLM) may need for a given (and/or present) context and/or given (and/or present) task. Thus, prompts may be kept narrow and specific to the context and/or to the task.

Alternatively or in addition, the context may change with each step taken by the user.

Multiple workflow cycles may be needed to execute an entire workflow.

In a (e.g., final) step, textual clinical concept algorithm (and/or LLM) output may go through the further network and/or further model (e.g., the AI-powered output classifier) to achieve the highest possible performance for the given (and/or present) context (and/or task) and provide safeguards and/or guard rails in case the textual clinical concept algorithm (and/or LLM) output is too variable or the textual clinical concept algorithm (and/or LLM) misunderstands the context and/or task, e.g., confusing the context of an aortic valve (AV) with the context of a mitral valve (MV), and/or of a pulmonary valve.

The at least one trained AI model may be trained based on training data comprising input training data and output training data.

The input training data may comprise medical image data sets from multiple medical imaging modalities comprising the first medical imaging modality and the at least one second medical imaging modality. Alternatively or in addition, the input training data may comprise textual guidelines in relation to the clinical workflow, in particular clinical guidelines, standard operating procedures (SOPs), and/or site-specific rules. Further alternatively or in addition, the input training data may comprise functional couplings among anatomical structures, and/or anatomical views, comprised in the medical image data sets.

The output training data may comprise results of user interactions in relation to the input medical image data sets.

The user interactions within the output training data may be obtained from application log files. Alternatively or in addition, the user interactions within the output training data may be correspond to annotations (and/or labels) of the medical image data sets comprised as input training data.

For training the one or more AI models, image variations may be made used of, e.g., by random withholding (e.g., still) frames and/or clips from an echo study with 100+ clips, and/or MRT sequences from a cardiac MRT, and/or reconstructions from a cardiac CT.

A clip may comprise a temporal sequence of frames, in particular covering the cardiac cycle. An echo study may (e.g., typically) comprise clips (and/or multi-frame) and/or images which are single-frame.

Spectral Doppler images may (e.g., typically) comprise single frame images consisting of a B-mode image showing the positioning and the wave form of the Doppler signal which covers multiple heart beats. Examples are provided in Table 6 of the "Guidelines for Performing a Comprehensive Transthoracic Echocardiographic Examination in Adults" [3], which is included herein by reference.

Alternatively or in addition, for training the one or more AI models, actual (also denoted as real) workflow examples may be made use of, e.g., comprising inter-operator variability (e.g., learning in which sequence, and/or order, a user executes one or more tasks and/or steps, and/or when the user needs one or more corresponding anatomical views, and/or images, vs. complementary anatomical views, and/or images).

Alternatively or in addition, for training the one or more AI models, permutations of workflow steps may be used.

Further alternatively or in addition, for training the one or more AI models, one or more (in particular multiple) clinical guidelines and/or multiple versions of the guidelines may be made use of. The clinical guidelines may in particular comprise a recommended (or prescribed) sequence, and/or order, of workflow steps and/or tasks.

The training of the one or more AI models may aim at maximizing a performance to identify the next workflow step and/or the most efficient execution of the overall workflow for a given clinical task.

In one embodiment, the at least one trained AI model may be trained offline, and/or before deployment (e.g., at a clinical site).

In another embodiment, the at least one trained AI model may (e.g., after an initial offline training) be trained online, e.g., using the received user input and/or monitoring for further user input and/or user feedback in response to the indication of the clinical workflow guidance.

The user input, user interaction, and/or user feedback may comprise a selection of one or more medical image data sets, and/or anatomical views, across multiple imaging modalities comprising the at least one second medical imaging modality and/or the first medical imaging modality. Alternatively or in addition, the user input, user interaction, and/or user feedback may comprise an alignment of an anatomical structure (also denoted as anatomy alignment) comprised in the first medical image data set and the at least one second medical image data set. E.g., a cardiovascular anatomy may be aligned "on axis" and/or "off axis".

A complete echo exam may comprise 2D images (and/or 2D medical image data sets) and/or clips with pre-defined views, e.g., as exemplified in Table 2 of the "Guidelines for Performing a Comprehensive Transthoracic Echocardiographic Examination in Adults" [3], which is included herein by reference.

The views may comprise (e.g., typical) anatomical landmarks and structures.

Positioning the transducer need not be easy, and/or there is always a chance that the user (e.g., clinician) who acquires the images (and/or medical image data sets) does not get the view exactly right (which may also be denoted as "off axis"). E.g., in apical views, the left ventricle may be (in particular inadvertently) foreshortened. Alternatively or in addition, a positioning of a view as planned (and/or as recommended by one or more clinical guidelines) may be denoted as "on axis".

The user input may be received by means of a user interface (UI), in particular by means of a graphical user interface (GUI).

The UI may comprise a computer mouse or trackpad. Alternatively or in addition, the GUI may comprise a touchscreen.

The UI, in particular the GUI, may comprise a display (e.g., the touchscreen).

The indication of the clinical workflow guidance may be output on a display, in particular on the display of the UI and/or GUI.

The method may further comprise a step of accessing a storage (also denoted as memory) for retrieving the at least one second medical image data set from a medical information system comprising at least one database for imaging and clinical data.

The medical information system, and/or the at least one database for imaging and clinical data, may comprise a cardiovascular imaging and information system (CVIS), a vendor neutral archive (VNA), a radiology information system (RIS), a picture archiving and communication system (PACS), and/or an electronic health record (HER).

The indication of the clinical workflow guidance may comprise a selection of a corresponding, to an anatomical view comprised in the first medical image data set, anatomical view of the at least one second medical image data set. Alternatively or in addition, the indication of the clinical workflow guidance may comprise a selection of a complementary, to an anatomical view comprised in the first medical image dataset, anatomical view of the at least one second medical image data set. Further alternatively or in addition, the indication of the clinical workflow guidance may comprise a (e.g., functionally coupled) complementary image, comprised in the at least one second medical image data set, indicative of a (in particular cardiac, and/or anatomic) function. Further alternatively or in addition, the indication of the clinical workflow guidance may comprise a recommendation to acquire one or more further medical image data sets. Still further alternatively or in addition, the indication of the clinical workflow guidance may comprise a recommendation for a next step in the clinical workflow, in particular for performing a measurement using the at least one second medical image data set.

The corresponding anatomical view (briefly: corresponding view) may comprise an alignment of one or more anatomical structures (and/or anatomy alignment) comprised in the first medical image data set and the at least one second medical image data set.

The complementary anatomical view (briefly: complementary view) may comprise a view on one or more anatomical structures comprised in the at least one second medical image data set, which differs from the anatomical view, in particular of the same one or more anatomical structures, provided by the first medical image data set.

The selection of the corresponding anatomical view, and/or of the complementary anatomical view of the at least one second medical data set to the anatomical view comprised in the first medical image data set may comprise displaying the (in particular two or more) anatomical views side by side.

The complementary image, indicative of the (in particular cardiac and/or anatomic) function, may comprise one or more anatomical structures in the at least one second medical image data set independently of the one or more anatomical structures comprised in the first medical image data set.

The selection of the complementary image, indicative of the (in particular cardiac and/or anatomic) function, may comprise displaying the selected complementary image together (e.g., side by side) with the first medical data set.

The cardiac function may comprise an ejection fraction (EF), in particular in relation to one or more of the cardiac chambers. Alternatively or in addition, the cardiac function may be assessed by means of Doppler (in particular Doppler US) imaging, and/or may be indicative of a pressure gradient (e.g., over a valve). Alternatively or in addition the pressure gradient may be (e.g., typically) measured over a valve, e.g., to determine the severity of aortic stenosis. Further alternatively or in addition, color Doppler on B-mode images may provide information on flow patterns, e.g., comprising (and/or indicative of) mitral valve regurgitation.

Further alternatively or in addition, the cardiac function may be assessed by means of (e.g., a value of the) FFR. Alternatively or in addition, FFR may be used to determine if a coronary stenosis is hemodynamically relevant and/or should be treated with an intervention or not.

The complementary image may be functionally coupled.

In an embodiment, the functional coupling of the complementary image may comprise (e.g., as the first medical image data set, and/or as the at least one second medical image data set) an anatomical image showing a cardiac function with wall motion in different myocardial segments. The functionally coupled complementary image may show a flow in the coronary artery which supplies the respective wall segments.

In a further embodiment, an anatomical image (e.g., as the first medical image data set, and/or as the at least one second medical image data set) shows aortic stenosis with, e.g., valve opening area. The (in particular functionally coupled) Spectral Doppler image (e.g., as the complementary image) may show the flow, or (e.g., flow) gradient, over the stenosis for the functional analysis.

The recommendation to acquire one or more further medical image data sets may comprise a recommendation relating to the first medical imaging modality, the at least one second medical imaging modality, and/or any further medical imaging modality. The further medical imaging modality may be available at a clinical site, where the clinical workflow guidance according to the inventive technique is performed. Alternatively, the further medical imaging modality may refer to a medical imaging modality not available at the clinical site, where the clinical workflow guidance according to the inventive technique is performed. E.g., the recommendation may comprise referring a patient to a different clinical site for acquiring one or more further medical image data sets by means of the further medical imaging modality.

The recommendation for performing the measurement may comprise, e.g., a measurement of a size of a cardiac chamber during a predetermined cardiac phase (e.g., diastolic and/or systolic, in particular end diastolic and/or end systolic).

The display of the one or more corresponding anatomical views, complementary anatomical views, and/or complementary images together (e.g., side by side) may be used for visual assessment by the user (e.g., medical practitioner and/or physician). The display of the one or more corresponding anatomical views, complementary anatomical views may also be denoted as anatomy alignment.

The term "anatomy alignment" may apply to (and/or may comprise) matching anatomical structures of interest using one or more corresponding and/or complementary views.

An example for anatomical alignment with one or more corresponding views comprise Apical 4-chamber (A4C) in echo and cardiac MRI.

An example for anatomical alignment with one or more complementary views may comprise that in 2D echo the aortic valve can be seen in a Parasternal Short Axis (PSAX) view on the level of the great vessels and in a Parasternal Long Axis (PLAX) view zoomed on the aortic valve. Alternatively or in addition, complementary views may be acquired using (and/or may be from) different imaging modalities.

The display, and/or the anatomy alignment, may be performed without performing measurements. For example, a patient's cardiac function may be analysed both quantitatively (e.g., by means of the EF) and/or qualitatively (e.g., visually) by reviewing wall motion across all cardiac segments.

According to a further embodiment, a medical practitioner (and/or physician) performing a final review of a procedure report may need to confirm that all findings are correct, e.g., that the patient's "left ventricular EF has decreased and there is new hypokinetic motion in the anterior wall." By the inventive technique, the relevant images from both current and prior exam(s) may be displayed (and/or shown). The one or more prior exams may comprise echo and/or MRT. The one or more image data sets may comprise apical 2 chamber (A2C) clips (in particular with or without contours for EF measurement), short axis (SAX) clips (e.g., for visual assessment), and/or clips with strain analysis.

A clip may comprise a temporal sequence (and/or multi-frame object, in particular covering the cardiac cycle).

For 2D strain, three views may be (e.g., typically) used: Apical 4 chamber (A4C), Apical 2 chamber (A2C) and Apical 3 chamber (A3C).

Alternatively or in addition, strain results from all three views may be shown on a single image together, e.g., with a polar plot showing strain results and/or other charts. The single image may be more relevant (and/or impactful) for a user (e.g., clinician) reviewing the study than looking at the three original clips.

As to a device aspect, a computing device for multi-modality medical image clinical workflow guidance is provided. The computing device comprises a first interface configured for receiving a user input in relation to a first medical image data set acquired by means of a first medical imaging modality. The computing device further comprises an assessment unit configured for assessing, by means of a clinical-concept-to-medical-image linking algorithm, the received user input in view of at least one second medical image data set acquired by means of at least one second medical imaging modality. The computing device still further comprises a second interface configured for outputting an indication of a clinical workflow guidance in relation to the at least one second medical image data set.

The computing device may be configured to perform any one of the steps, or comprise any one of the features, described in the context of the method aspect.

As to a system aspect, a system for multi-modality medical image clinical workflow guidance is provided. The system comprises one or more computing devices according to device aspect. The system further comprises storage (and/or memory) configured for storing medical image data sets acquired from multiple medical imaging modalities. The storage (and/or memory) may be accessible by (in particular an optional third interface of) the one or more computing devices for retrieving at least one second medical image data set from a medical information system comprising at least one database for imaging and clinical data.

The system still further comprises a UI, in particular a GUI, for forwarding one or more user inputs to the first interface of the one or more computing devices. The UI, in particular GUI, is further configured for outputting one or more indications, received from the second interface of the one or more computing devices, to the user.

As to a further aspect, a computer program product is provided. The computer program product comprises program elements which induce a computing device (e.g., the computing device according to the device aspect) to carry out the steps of the method for multi-modality medical image clinical workflow guidance according to the method aspect, when the program elements are loaded into a memory (and/or storage) of the computing device.

As to a still further aspect, a computer-readable medium is provided. On the computer-readable medium, program elements are stored that can be read and executed by a computing device (e.g., the computing device according to the device aspect), in order to perform steps of the method for multi-modality medical image clinical workflow guidance according to the method aspect, when the program elements are executed by the computing device.

The properties, features and advantages of this invention described above, as well as the manner they are achieved, become clearer and more understandable in the light of the following description and embodiments, which will be described in more detail in the context of the drawings.

This following description does not limit the invention on the contained embodiments. Same components or parts can be labeled with the same reference signs in different figures. In general, the figures are not for scale.

It shall be understood that a preferred embodiment of the present invention can also be any combination of the dependent claims or above embodiments with the respective independent claim.

These and other aspects of the invention will be apparent from and elucidated with reference to the embodiments described hereinafter.

BRIEF DESCRIPTION OF THE DRAWINGS

FIGS. 5A and 5B shows a further illustrative example of using a first medical image data set acquired by means of CT and a second medical image data set acquired by means of TTE, respectively, for assessing a patient's aortic stenosis, wherein the views, and/or images, of the second medical image data set are selected for display by means of the method of FIG. 1;

FIG. 7 schematically illustrates a further example of jointly training a clinical-concept-to-medical-image linking algorithm using a further network and/or further model (e.g., denoted as AI-powered orchestrator) data-connecting the semantic image understanding algorithm and the textual clinical concept algorithm.

Any reference signs in the claims should not be construed as limiting the scope.

Figure 1:
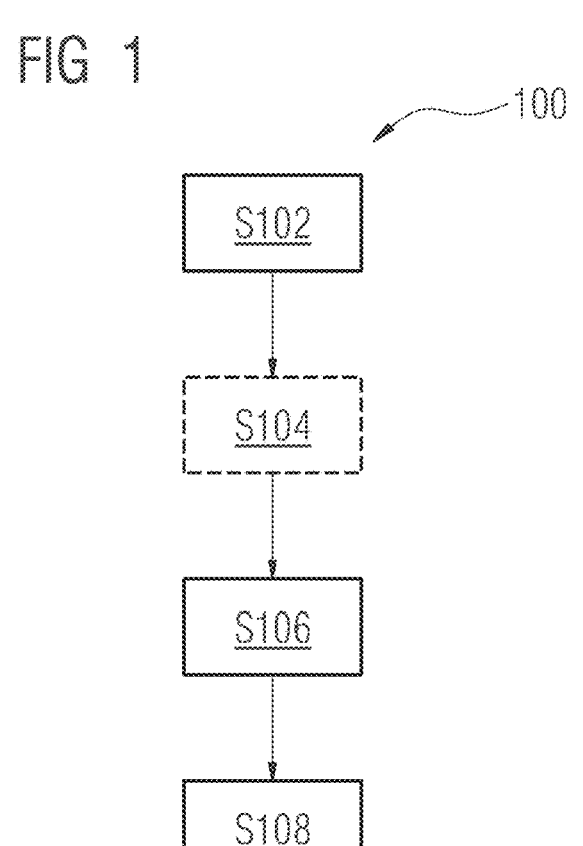
FIG. 1 is a flow chart of a method for multi-modality medical image clinical workflow guidance according to a preferred embodiment of the present invention.

FIG. 1 schematically illustrates an exemplary flowchart of a computer-implemented method for multi-modality medical image clinical workflow guidance. The method is generally referred to by the reference sign 100.

The method 100 comprises a step S102 of receiving a user input in relation to a first medical image data set acquired by means of a first medical imaging modality.

The method 100 further comprises a step S106 of assessing, by means of a clinical-concept-to-medical-image linking algorithm, the received S102 user input in view of at least one second medical image data set acquired by means of at least one second medical imaging modality.

The method 100 further comprises a step S108 of outputting an indication of a clinical workflow guidance in relation to the at least one second medical image data set.

Optionally, the method 100 comprises a step S104 of accessing a storage (also denoted as memory) for retrieving the at least one second medical image data set from a medical information system comprising at least one database for imaging and clinical data.

Figure 2:
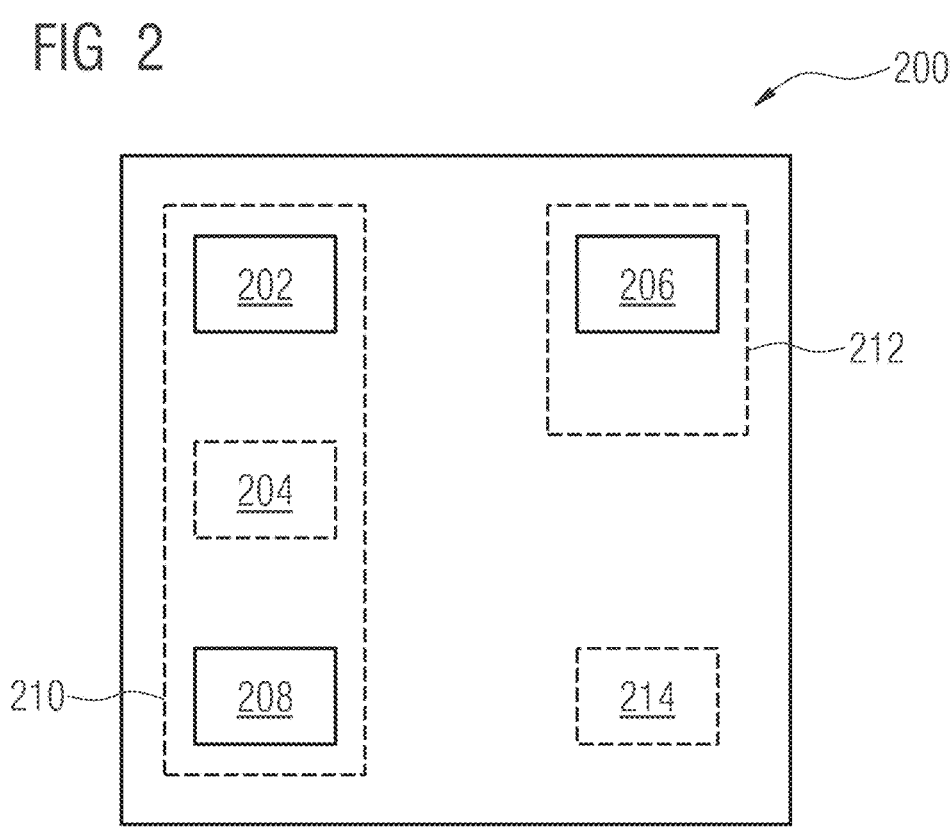
FIG. 2 is an overview of the structure and architecture of a computing device for multi-modality medical image clinical workflow guidance according to a preferred embodiment of the present invention.

FIG. 2 schematically illustrates an exemplary architecture of a computing device for multi-modality medical image clinical workflow guidance. The computing device is generally referred to by the reference sign 200.

The computing device 200 comprises a first interface 202 configured for receiving a user input in relation to a first medical image data set acquired by means of a first medical imaging modality.

The computing device 200 further comprises an assessment unit 206 configured for assessing, by means of a clinical-concept-to-medical-image linking algorithm, the received user input in view of at least one second medical image data set acquired by means of at least one second medical imaging modality.

The computing device 200 further comprises a second interface 208 configured for outputting an indication of a clinical workflow guidance in relation to the at least one second medical image data set.

Optionally, the computing device 200 comprises a third interface 204 configured for accessing a storage (also denoted as memory) for retrieving the at least one second medical image data set from a medical information system comprising at least one database for imaging and clinical data.

Any one of the first interface 202, the second interface 208 and the optional third interface 204 may be comprised in an input-output interface.

The computing device 200 may further comprise a processor 212 and/or at least one memory (and/or storage) 214. The assessment unit 206 may be comprised in, or may be embodied by, the processor 212.

The computing device 200 may be configured for performing the method 100.

A system for multi-modality medical image clinical workflow guidance may comprise the computing device 200 (or multiple computing devices 200). The system may further comprise a storage (also denoted as memory) configured for storing medical image data sets acquired from multiple medical imaging modalities. The storage may be accessible by (in particular the third interface 204 of) the computing device 200 (or one or more of the multiple computing devices 200) for retrieving at least one second medical image data set from a medical information system comprising at least one database for imaging and clinical data.

The system may still further comprise a UI, in particular a GUI. The UI, in particular the GUI, may be configured for forwarding one or more user inputs to the first interface 202 of the computing device 200 (or to one or more of the multiple computing devices 200). The UI, in particular GUI, may be further configured for outputting, to the user, one or more indications received from the second interface 208 of the computing device 200 (or from one or more of the multiple computing devices 200).

The inventive technique (e.g., comprising the method 100, and/or the computing device 200) comprises a clinical-concept-to-medical-image linking algorithm, which may comprise a textual clinical concept algorithm (also denoted as large language model, LLM) and a semantic image understanding algorithm (which may alternatively be denoted as semantic image extraction algorithm, and/or as semantic image relationship algorithm, and/or may be abbreviated as SIU), which may be in (e.g., indirect and/or direct) data connection to a medical imaging and information system comprising at least one database for imaging and clinical data.

Figure 3:
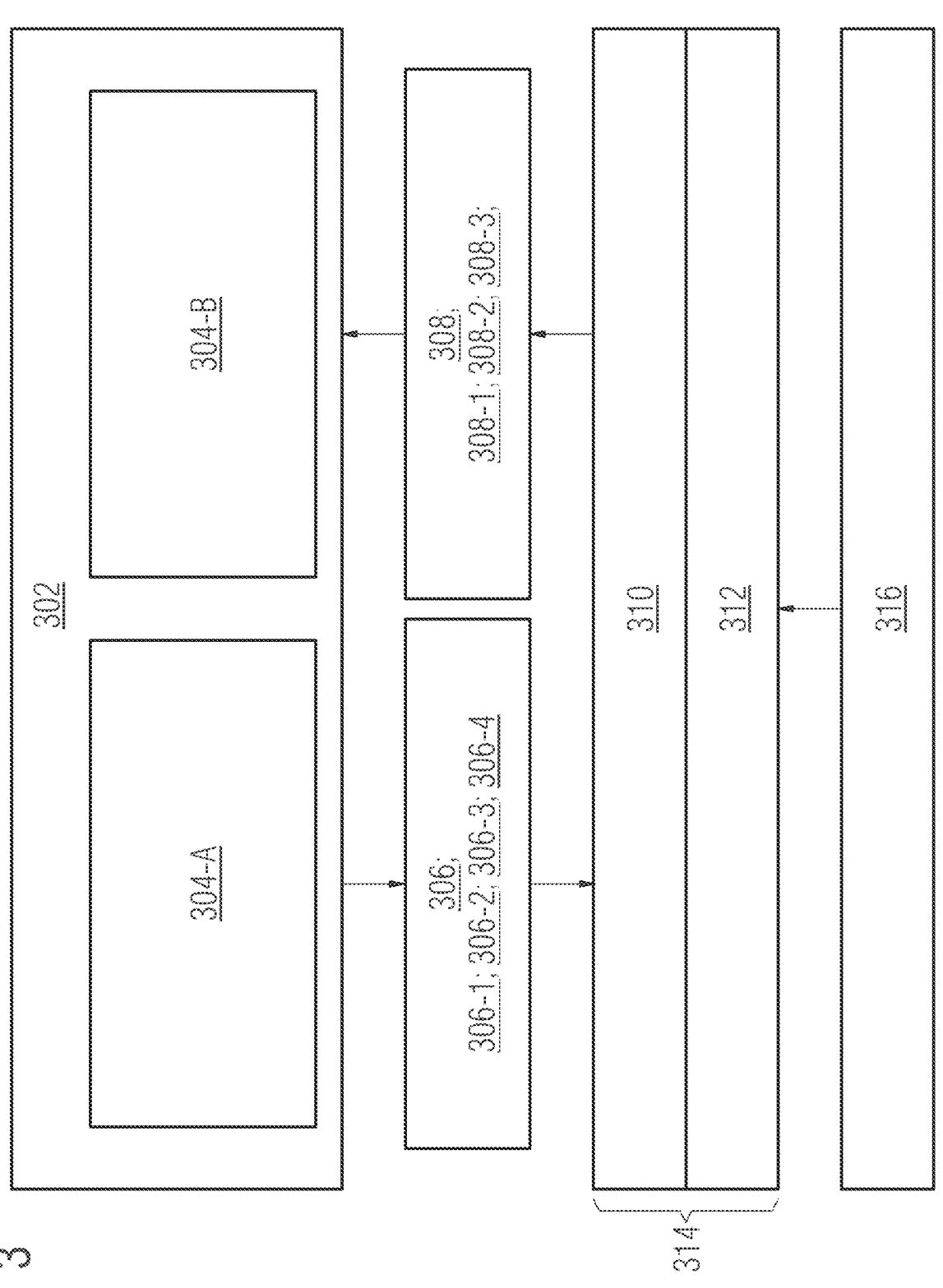
FIG. 3 shows an exemplary data flow between a medical imaging and information system comprising multiple medical imaging modalities and a clinical-concept-to-medical-image linking algorithm according to the method of FIG. 1.

FIG. 3 shows an exemplary medical imaging and information system at reference sign 302. The medical imaging and information system 302 in FIG. 3 may in particular be a cardiovascular medical imaging and information system.

The medical imaging and information system 302 in FIG. 3 comprises at least one database for imaging and clinical data acquired from a (in particular cardiovascular) first medical imaging modality 304-A and a (in particular cardiovascular) second medical imaging modality 304-B. The medical imaging and information system 302, in particular the at least one database for imaging and clinical data, may comprise data acquired from further medical imaging modalities (not shown in FIG. 3).

At reference sign 306, a review of a first medical image data set acquired from the first medical imaging modality 304-A is performed. Alternatively or in addition, from the first medical imaging modality 304-A (e.g., from a first medical image data set acquired by means of the first medical imaging modality 304-A), one or more types of information may be extracted at reference sign 306. The one or more types of information may comprise a clinical context 306-1, one or more images (e.g., as 2D projections, and/or 2D slices, of a 3D first medical image data set, and/or still frames out of a cine series) 306-2, measurements 306-3, and/or user interactions (also denoted as user inputs) 306-4 when reviewing multi-modality (e.g., cardiovascular) studies.

The one or more types of information 306; 306-1; 306-2; 3063; 306-4 are provided to a clinical-concept-to-medical-image linking algorithm 314. In FIG. 3, the clinical-concept-to-medical-image linking algorithm 314 is shown to comprise a semantic image understanding algorithm (also abbreviated as SIU) 310 and a textual clinical concept algorithm (also denoted as large language model, LLM) 312.

As shown at reference sign 316, the clinical-concept-to-medical-image linking algorithm 314 of FIG. 3 is provided with one or more clinical guidelines.

At reference sign 308, a selection of at least one second medical image data set is performed by the clinical-concept-to-medical-image linking algorithm 314 and based on the input information 306 in relation to the first medical image data set as well as based on the clinical guidelines 316. Alternatively or in addition, an image selection 308-1, an anatomy alignment 308-2, and/or a next workflow step 308-3 is determined (and/or predicted) in relation to the at least one second medical imaging modality 304-B.

The textual clinical concept algorithm (and/or LLM) driven system of FIG. 3 can be used for multi-modality cardiovascular analysis (which may also be denoted as Cardiovascular Anatomy LLM).

The inventive technique (e.g., comprising the method 100, and/or computing device 200), as schematically illustrated in FIG. 3, is based on a tandem approach of the textual clinical concept algorithm (and/or LLM) 312 and semantic image understanding algorithm (also denoted as semantic image understanding AI model) 310 working together. The textual clinical concept algorithm (and/or LLM) 312 in the example of FIG. 3 processes clinical context information (e.g., comprised in the metadata of the respective medical image data set), and the semantic image understanding algorithm 310 provides a detailed understanding of image content (in particular of the same medical image data set as analysed, and/or processed, by the textual clinical concept algorithm).

The inventive technique (e.g., comprising the method 100, and/or computing device 200) can be applied to predict image selection and/or anatomy alignment for medical images (and/or medical image data set) from multiple medical imaging modalities. Alternatively or in addition, the inventive technique (e.g., comprising the method 100, and/or computing device 200) can be used to predict the next step in a multi-modality medical image review. The clinical-concept-to-medical-image linking algorithm 314 (and/or the inventive system comprising the computing device 200) can learn from large amounts of multi-modality medical image data, clinical guidelines and/or large amounts of user inputs (also denoted as user interactions) during review of the multi-modality medical images (and/or medical image data sets), in particular in a cardiovascular information system.

The clinical-concept-to-medical-image linking algorithm 314 (and/or the inventive system comprising the computing device 200) is able to support a wide range of clinical questions as typically encountered in the workload handled by a CVIS.

The user input (and/or user interactions) of one or more users (e.g., clinicians) working with multi-modality medical images may comprise the selection of medical images for side-by-side comparison across medical imaging modalities, alignment of cardiovascular anatomy for comparison, and/or clinical measurements.

The one or more users (e.g., clinicians) may follow a protocol when reviewing imaging studies and adapt (e.g., the selection of medical images, alignment, and/or measurement) based on one or more clinical questions of the specific case, and/or in relation to a specific patient, and/or their treatment. Alternatively or in addition, a clinical question (e.g., relating to aortic stenosis, and/or myocarditis) may drive the selection of applicable clinical guidelines, and/or relevant parts within the guidelines.

The user input (and/or user interactions) comprises user's step-wise patterns and may be gathered, e.g., from a combination of application log files and (e.g., corresponding) image data sets, images, and/or anatomical views.

The input of a (e.g., the first, and/or at least one second) medical image data set may be analysed using semantic image understanding of the cardiovascular anatomy with a semantic image understanding algorithm (and/or semantic image understanding AI model) 310.

The semantic image understanding of available multi-modality medical image data sets, and/or measurements made by AI, and/or by a user, may be used to prompt the textual clinical concept algorithm (and/or LLM) 312. Each time a new measurement is made, and/or an existing measurement is edited, by the user, the prompt to the textual clinical concept algorithm (and/or LLM) 312 may change.

Each medical imaging modality (and/or imaging method) has its strengths and limitations. Measurements can be done in 2D and/or 3D. Moreover, there are no uniform methods of measurement of aortic root and aorta.

Review of (in particular cardiovascular) medical image data sets (also denoted as medical imaging studies) from a single medical imaging modality usually follows a standard protocol. Additional steps may be required based on the clinical question, and/or task. The workflow becomes much more complex when reviewing medical image data sets from multiple medical imaging modalities.

There are some image registration and/or fusion solutions for specific use cases, which may require special conditions to be met, such as, the presence of a TEE probe during an intervention.

Understanding the patterns of medical image review steps can help to develop AI models (also denoted as AI systems) which support users by predicting the next workflow steps and improving efficiency.

The inventive technique (e.g., comprising the method 100 and/or the computing device 200) helps the user (e.g., medical practitioner, physician, clinician, radiologist, and/or radiation oncologist) review multi-modality (in particular cardiovascular) medical image data sets in a more intuitive and efficient manner so that he or she can focus on image interpretation rather than search and image display manipulations.

The textual clinical concept algorithm (and/or LLM) 312 may predict (and/or propose, and/or determine) a medical image data set selection for next step in the workflow. Alternatively or in addition, the textual clinical concept algorithm (and/or LLM) 312 may predict (and/or propose, and/or determine) an anatomy alignment for images from multiple modalities.

The textual clinical concept algorithm (and/or LLM) 312, in tandem with the semantic image understand algorithm (and/or SIU) 310, can determine if there are sufficient or insufficient medical image data sets available (e.g., stored in a medical information system) to answer a given clinical question.

The inventive technique (e.g., comprising the method 100 and/or the computing device 200) enables prediction (and/or proposal, and/or determination) of medical image data set selection, of cardiac anatomy alignment and/or of the next workflow step in a flexible way based on the one or more clinical questions, deep understanding of the available medical image data sets and understanding of the relevant parts of applicable guidelines (e.g., comprising decision pathways).

The semantic image understanding algorithm (and/or SIU) 310 may be configured for automated image preparation in cardiovascular imaging workflows. Alternatively or in addition the semantic image understanding algorithm (and/or SIU) 310 may comprehensively analyse medical image data set content for semantic image understanding from entire cardiovascular imaging studies to create metadata for workflow enabling and automation.

The metadata of a medical image data set may comprise a view classification, e.g., main views, such as Apical 4 chamber (A4C), and/or sub-types of views. Alternatively or in addition, the metadata of the medical image data set may comprise anatomical landmarks, e.g., mitral valve (MV) 1, MV 2, True left ventricle (LV) Apex, and/or tricuspid valve 1. Further alternatively or in addition, the metadata of the medical image data set may comprise anatomical structures, e.g., LV, left atrium (LA), right ventricle (RV), right atrium (RA), and/or MV. Further alternatively or in addition, the metadata of the medical image data set may comprise a zoom level, e.g., a zoomed view. Further alternatively or in addition, the metadata of the medical image data set may comprise a cardiac phase identification, e.g., end diastole and/or end systole for each cardiac cycle in a temporal sequence of images (and/or, in particular still, frames) and/or clip comprised in the medical image data set. Further alternatively or in addition, the metadata of the medical image data set may comprise an indication of a contrast, e.g., a presence of contrast enhancement in the LV. Further alternatively or in addition, the metadata of the medical image data set may comprise an image quality assessment, e.g., a noise level, image artifacts, and/or image quality for each relevant cardiac structure such as LV, and/or RV. Further alternatively or in addition, the metadata of the medical image data set may comprise a score for use cases, e.g., assigning a score for suitable use cases. The assignment of the score may be based on an image quality, e.g., at specific phases in the cardiac cycle, and/or anatomical structures included in the medical image data set. Alternatively or in addition, (e.g., regarding the assignment of the score being based on an image quality) if both LV and LA are present (e.g., within a clip and/or an image), and there is good image quality for the LV and compromised quality for the LA, the use of the clip and/or image may depend on the clinical context and/or question. E.g., the clip and/or image may be used to answer LV related questions, but not LA related questions.

In contrast to conventional approaches in the literature on AI-based cardiac view classification, the inventive technique (e.g., comprising the method 100 and/or the computing device 200) provides a richer set of semantic information derived from medical image data sets, which may be used to perform subsequent steps.

The inventive technique (e.g., comprising the method 100 and/or the computing device 200) can be much more flexible than conventional techniques, including conventional techniques on semantic image understanding, by avoiding the need for (in particular manually) pre-defined rules, which, e.g., conventionally involve high efforts to design and maintain.

Alternatively or in addition, the inventive technique (e.g., comprising the method 100 and/or the computing device 200) can make much wider use of textual data, such as clinical guidelines (e.g., checking if all, and/or sufficient, medical image data sets are acquired for the clinical question) and clinical context (e.g., aortic stenosis assessment where the application shows all relevant echo image data sets to assess the aortic valve, AV) not available in conventional techniques.

E.g., the relevant echo image data sets may comprise a SAX view on the level of the great vessels, a parasternal long axis (PLAX) view zoomed on the AV, and/or a Doppler flow evaluation of the AV.

Alternatively or in addition, by the inventive technique (e.g., comprising the method 100 and/or the computing device 200, relevant images for LV function assessment (e.g., low flow, and/or low gradient aortic stenosis in case of reduced EF) may be selected for display (and/or shown), e.g., comprising A4C and/or A2C.

The clinical-concept-to-medical-image linking algorithm 314 may be trained to learn from situations where the user (e.g., a clinician) is focused on a review of a corresponding (in particular cardiovascular) anatomy, e.g., comprising the AV in cardiac CT and/or a PSAX view on the level of the large vessels in 2D echocardiography.

The (e.g., cardiovascular) anatomical concepts across medical imaging modalities (e.g., CT and US) may be defined in a universal way without resorting to modality-specific terms.

Alternatively or in addition, the clinical-concept-to-medical-image linking algorithm 314 may learn situations where the user (e.g., a clinician) is interested in complementary views, e.g., for evaluation of coronary arteries using cardiac CT angiography (CTA) and myocardial function evaluation using medical image data sets which display the segments supplied by a given coronary artery.

The complementary views may be derived by functional coupling and/or association between two anatomical entities. E.g., the coronary arteries from CTA may be coupled with the myocardium (e.g., for an assessment of wall motion) via a functional relationship of myocardial perfusion.

In another embodiment of the inventive technique (e.g., comprising the method 100 and/or the computing device 200), the training of the clinical-concept-to-medical-image linking algorithm 314 may be performed offline without requiring any log files from the clinical usage of a multi-modality (in particular cardiac) reading. The offline training may be achieved by annotating medical image data sets of multiple (in particular cardiac) medical imaging modalities using the same semantic set of labels (and/or annotations) across the (in particular cardiac) medical imaging modalities.

The complementary views may be pre-defined for various known functional relationships between (in particular cardiac) anatomical entities.

When using the inventive technique (e.g., comprising the method 100 and/or the computing device 200), instructions may be provided by the user in semantic form, e.g., "show the corresponding SAX views at the level of the MV in the latest available cardiac CT and echocardiography study and align the images". Alternatively or in addition, the instructions may be provided through user interactions and then guided by the clinical-concept-to-medical-image linking algorithm 314, e.g., predicting the next step that the user is expected to (e.g., according to clinical guidelines, and/or wants) to take.

Based on understanding the clinical context (e.g., comprising a reason for a patient's exam), available medical image data sets and/or existing measurements, the clinical-concept-to-medical-image linking algorithm 314 may predict (and/or determine, and/or propose) which measurements to make and guide the user in their clinical workflow, and/or in their sequence.

The clinical-concept-to-medical-image linking algorithm 314 may be designed in an adaptive manner to learn from user feedback.

Usage of the inventive technique (e.g., comprising the method 100 and/or the computing device 200), in particular comprising the clinical-concept-to-medical-image linking algorithm 314, can lead to a more efficient review of multi-modality (in particular cardiovascular) medical image data sets across a wide range of clinical questions and/or tasks. Alternatively or in addition, the use of the inventive technique (e.g., comprising the method 100 and/or the computing device 200), in particular comprising the clinical-concept-to-medical-image linking algorithm 314, can lead to increased diagnostic accuracy by making multi-modality information easier to analyze. Further alternatively or in addition, the use of the inventive technique (e.g., comprising the method 100 and/or the computing device 200), can enhance consistency across users (e.g., medical practitioners, physicians, clinicians, radiologists, and/or radiation oncologists) in a clinical department or across hospitals.

Products supporting the analysis of multi-modality cardiovascular images can benefit from the inventive technique (e.g., comprising the method 100 and/or the computing device 200).

In one embodiment of the invention, the system analyses whether 2D views (e.g., defined by one or more landmarks and their relations) are "on axis" or "off axis" as per clinical guidelines, e.g., foreshortened apical views in echocardiography.

Figures 4A, 4B:
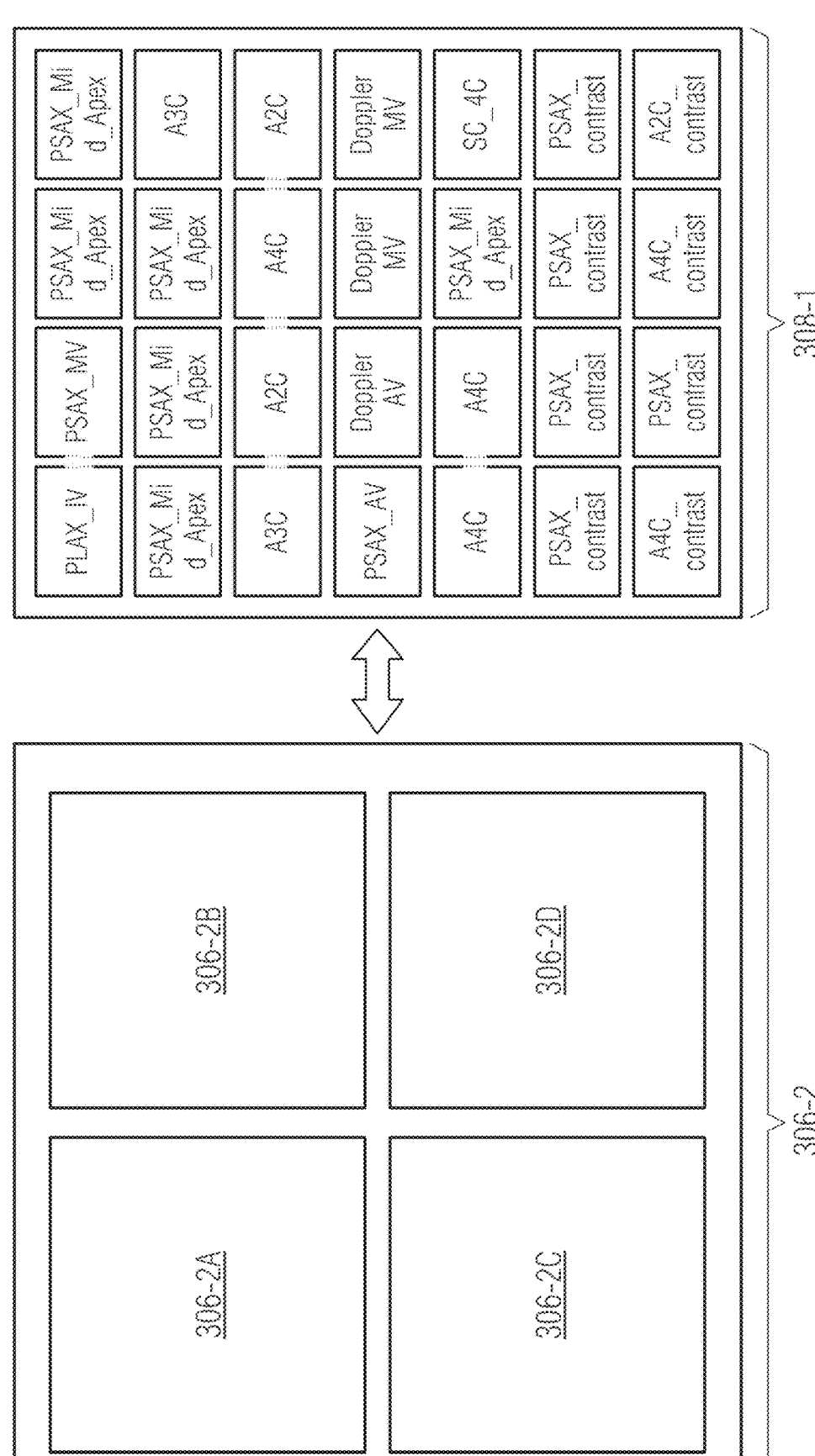
FIGS. 4A and 4B show an illustrative example of using a first medical image data set acquired by means of CT and a second medical image data set acquired by means of TTE, respectively, for evaluating a patient's cardiac function, wherein the views, and/or images, of the second medical image data set are selected for display by means of the method of FIG. 1.

FIGS. 4A and 4B schematically illustrate an exemplary use of the inventive technique with two different medical imaging modalities comprising the first medical (in particular cardiovascular) imaging modality 304-A, providing one or more (e.g., 3D) cardiac CT image data sets as one or more first image data sets 306-2, and the second medical (in particular cardiovascular) imaging modality 304-B, providing a (e.g., 2D) TTE study with 100+ clips (and/or temporal sequences) sorted by image acquisition sequence as the second medical image data set 308-1.

Conventionally, combining analysis of the one or more (e.g., 3D) cardiac CT image data sets 306-2 and (e.g., 2D) TTE study image data set 308-1 presents a challenge when the user (e.g., medical practitioner, physician, clinician, radiologist, and/or radiation oncologist) wants to work efficiently with multi-modality images. E.g., the steps, and/or image selection, performed by the user may be too rigid, and/or many manual steps may be required until the first 306-2 and second 308-1 medical image data sets are ready side by side.

The cardiac CT study 306-2 in the example of FIG. 4A comprises a cardiac CT image 306-2A focused on the AV in the sagittal view, a cardiac CT image 306-2B focused the on AV in the coronal view, a cardiac CT image 306-2C focused on the AV in the axial view, and a cardiac CT image 306-2D focused on AV volume rendering technique (VRT) view 306-2D.

Any cardiac CT image 306-2A; 306-2B; 306-2C; 306-2D may comprise, or may correspond to, a 2D projection (and/or 2D slice) of a 3D cardiac CT image data set.

FIG. 4B schematically illustrates the TTE study with 100+ clips sorted by acquisition sequence as the second medical image data set 308-1 with different views, and/or (e.g., still) frames, selected for side by side display with the cardiac CT images 306-2A; 306-2B; 306-2C; 306-2D of FIG. 4A.

The denomination of the potential views, and/or (e.g., still) frames, of the (in particular 2D) TTE views, (e.g., still) frames, and/or images listed in FIG. 4B is summarized in the table below.

| Abbreviations for TTE views (and/or images) in FIG. 4B | |
| --- | --- |
| A2C | Apical 2 chamber view |
| A3C | Apical 3 chamber view |
| A4C | Apical 4 chamber view |
| A5C | Apical 5 chamber view |
| PSAX | Parasternal short axis |
| PLAX | Parasternal long axis |
| AV | Aortic valve |
| MV | Mitral valve |
| SC | Subcostal |

PSAX_Mid_Apex (e.g., as displayed in FIG. 4B) may comprise a category which includes PSAX Mid or/and PSAX Apex. Alternatively or in addition, PSAX mid comprise imaging (and/or may be) at the level of the papillary muscles.

FIG. 4B shows an example where some (e.g., predetermined) views are grouped into categories. In an alternative embodiment (not shown), the group (and/or grouped categories) may be separated into PSAX Mid and PSAX Apex.

Contrast enhancement may be used to optimize image quality, in particular using the same views with and without contrast, e.g. A4C and A2C. Contrast views may be acquired at the end of the study, meaning that A4C without and with contrast are not sequentially arranged in a study in which images an/or clips are displayed in the sequence of acquisition.

As an example, A4C is displayed on the third and fifth lines in FIG. 4B, and A4C_contrast is displayed on the last (and/or seventh) line in FIG. 4B.

Alternatively or in addition, in echo studies, a user (e.g., clinician) may take several clips with the same view, e.g., in situations where patient factors make it hard to achieve good image quality. A sonographer may try different techniques to get the best image quality possible and keep them (e.g., all acquired images) in the study to give the user (e.g., clinician and/or physician) a choice of clips to evaluate, e.g., cardiac function.

FIGS. 5A and 5B schematically illustrate a further exemplary use of the inventive technique with two different medical imaging modalities comprising the first medical in particular cardiovascular) imaging modality 304-A, providing a (e.g., 3D) cardiac CT image data set as the first image data set 306-2, and the second medical (in particular cardiovascular) imaging modality 304-B, providing a (e.g., 2D) TTE study as the second medical image data set 308-1.

For aortic stenosis (AS) assessment (and/or measurement), multi-modality medical imaging is very common, e.g., comprising one or more 2D TTE echo exams for diagnosis and severity assessment, and 3D TEE and/or cardiac CT for procedure planning measurements.

A valve anatomy needs to be assessed usually, e.g., a number of cusps (in particular 2 or 3), cusp mobility, commissural fusion, and/or valve calcification in the context of AS assessment.

For AS assessment (and/or measurement), usually, multiple measurements need to be made and analysed. E.g., AV area (which is more difficult in case of a calcified valve), a AS jet velocity (e.g., using Doppler), a LV outflow tract (LVOT) velocity, and/or a cardiac EF (e.g., as a low flow AS needs to be assessed correctly) need to be measured.

The user (e.g., medical practitioner, physician, clinician, radiologist, and/or radiation oncologist) may be required (and/or may want) to look at a cardiac CT and corresponding anatomical views, complementary anatomical views, and/or complementary images from echo with different views, and/or different information when following a particular guideline. Alternatively or in addition, the selection of medical image data sets, images, and/or views for the AS assessment may depend on which medical image data sets are available with good quality (e.g., "on axis", and/or with adequate image quality).

For AS assessment (and/or measurement), the workflow, in particular, comprising next steps, is logical, but non-trivial to predict (and/or determine, and/or propose). There may exist several valid options, e.g., based on a user's reference.

FIG. 5A schematically illustrates a cardiac CT image data set 306-2 with focus on the AV for AS assessment. The user can change the view orientation as needed in the 3D dataset.

FIG. 5B schematically illustrates a series of views, and/or images, from a 2D TTE clip (and/or temporal sequence) 308-1 for the AS assessment in connection with FIG. 5B.

In FIG. 5B, the 2D TTE PSAX view of the level of the AV 308-1A is the corresponding anatomical view (also denoted as cardiovascular view) to the cardiac CT image data set 306-2 of FIG. 5A.

In FIG. 5B, complementary anatomical views, providing different perspectives, to the cardiac CT image data set 306-2 of FIG. 5A comprise a 2D TTE PLAX view of the LV 308-1B, a 2D TTE PLAX view zoomed on the AV 308-1C, a 2D TTE A3C view 308-1D, and a 2D TTE A3C view with contrast 308-1E.

In FIG. 5B, further an example of a complementary image to the cardiac CT image data set 306-2 of FIG. 5A, a 2D TTE Doppler image of the AV 308-1F, is schematically illustrated. The complementary images may provide different type of information, e.g., the Doppler showing the flow through the AV.

In FIG. 5B, further complementary images (and/or related images), a 2D TTE A4C view 308-1G and a 2D TTE ARC view 308-1H, are schematically illustrated. AS assessment may vary by cardiac function, e.g., if there is low flow, the gradients may need to be interpreted differently. E.g., determining a patient's biplane EF will require A4C and A2C view.

Aortic stenosis measurements (e.g., of the aortic annulus) are important, e.g., for valve sizing in transcatheter AV replacement (TAVR).

There exist numerous medical guidelines and/or clinical guidelines, e.g., issued by the American College of Cardiology Foundation, the American Association for Thoracic Surgery, the Society for Cardiac Angiography and Interventions, the Society of Thoracic Surgeons, and/or the Society of Cardiovascular Computed Tomography.

E.g., the "Recommendations for Cardiac Chamber Quantification by Echocardiography in Adults: An Update from the American Society of Echocardiography and the European Association of Cardiovascular Imaging" by Roberto M. Lang et al. [2] and the "Guidelines for Performing a Comprehensive Transthoracic Echocardiographic Examination in Adults: Recommendations from the American Society of Echocardiography" by Carol Mitchell et al. [3], both of which are included herein by reference, are pertinent, and/or highly relevant, for multi-modality medical image clinical workflow guidance, when evaluating cardiac, and/or cardiovascular, properties and/or functions.

Each guideline may have one or more different decision algorithms with different thresholds based on multiple parameters. Alternatively or in addition, the guidelines often comprise multi-step decision pathways.

An exemplary complex relationship between a medical image data set content and guidelines comprises an aortic root, which is a geometrically complex anatomy with four (4) sites for measurement of the aortic root and ascending aorta in 2D TTE (cf., e.g., Figure 10A and B of the "Recommendations" by Roberto M. Lang et a. [2]).

A further exemplary complex relationship between a medical image data set content and guidelines comprises correct and incorrect measurements, e.g., oblique annular measurements (cf., e.g., Figure 12C of the "Recommendations" by Roberto M. Lang et a. [2]).

A further exemplary complex relationship between a medical image data set content and guidelines comprises that the size of the aortic annulus varies by cardiac phase (e.g., midsystole vs. diastole). The semantic image understanding algorithm 310 may, e.g., provide the information on the size of the aortic annulus by cardiac phase to prompt the textual clinical concept algorithm (and/or LLM) 312.

A still further exemplary complex relationship between a medical image data set content and guidelines comprises that a calcified aortic annulus may impact measurements and impact which medical image data sets, anatomical views, and/or complementary images the user wants to use in the clinical workflow.

Figure 6:
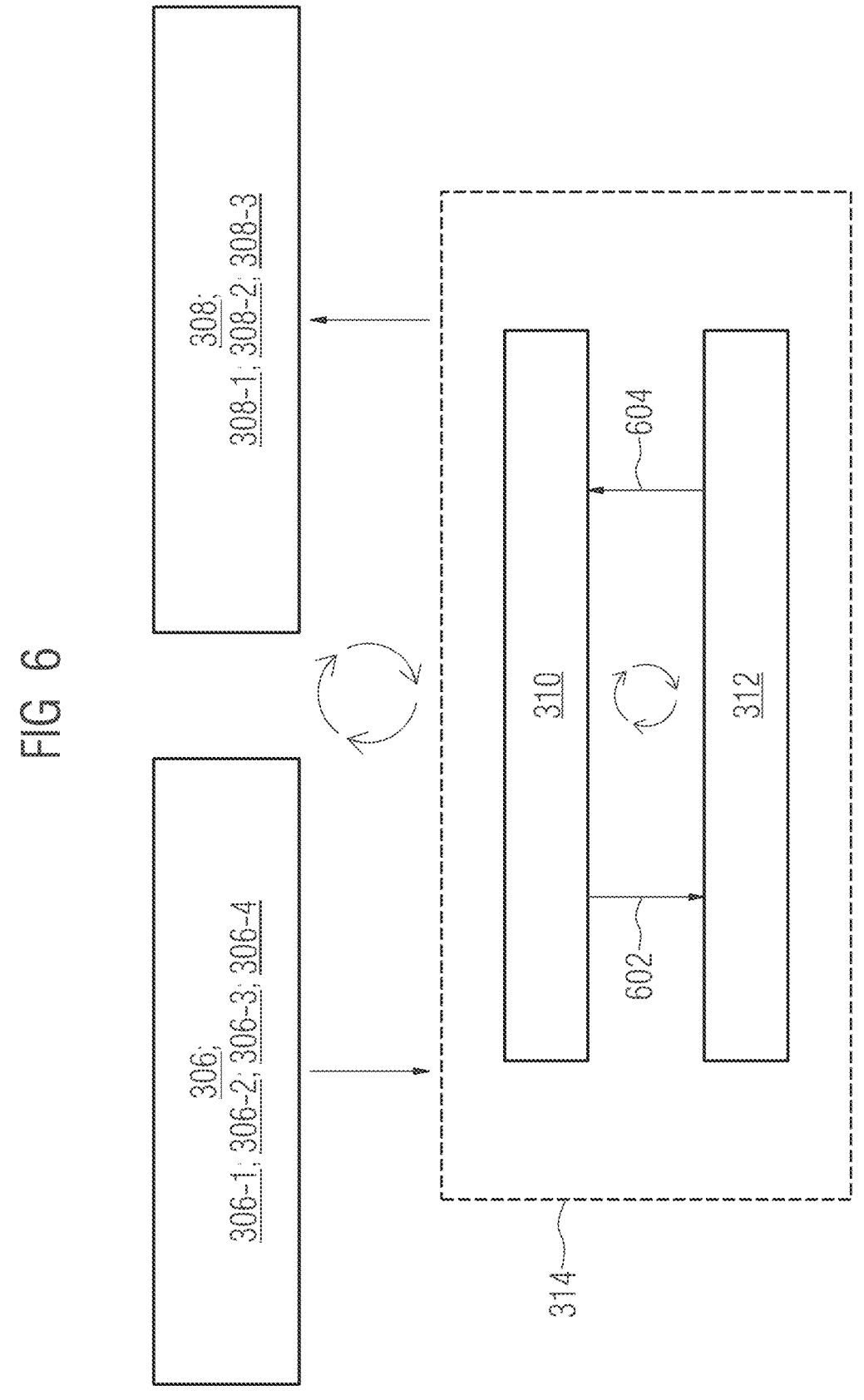
FIG. 6 schematically illustrates an example of jointly training a clinical-concept-to-medical-image linking algorithm iteratively and/or continuously using prompts and queries between a semantic image understanding algorithm and a textual clinical concept algorithm.

FIG. 6 schematically illustrates a first exemplary realization of joint training for the semantic image understanding algorithm 310 and the textual clinical concept algorithm 312 comprised in the clinical-concept-to-medical-image linking algorithm 314. In the example of FIG. 6, the semantic image understanding algorithm 310 and the textual clinical concept algorithm 312 are connected by iterative and/or continuous mini-cycles of queries 604 and prompts 602. The iterative and/or continuous cycle may have narrow and/or specific prompts. The prompts 602 may comprise a subset of available semantic image understanding (and/or SIU) information as relevant for the present context 306-1 and/or task. Alternatively or in addition, the mini-cycles may start with a query 604 based on the present context 306-1 and/or task.

Figure 7:
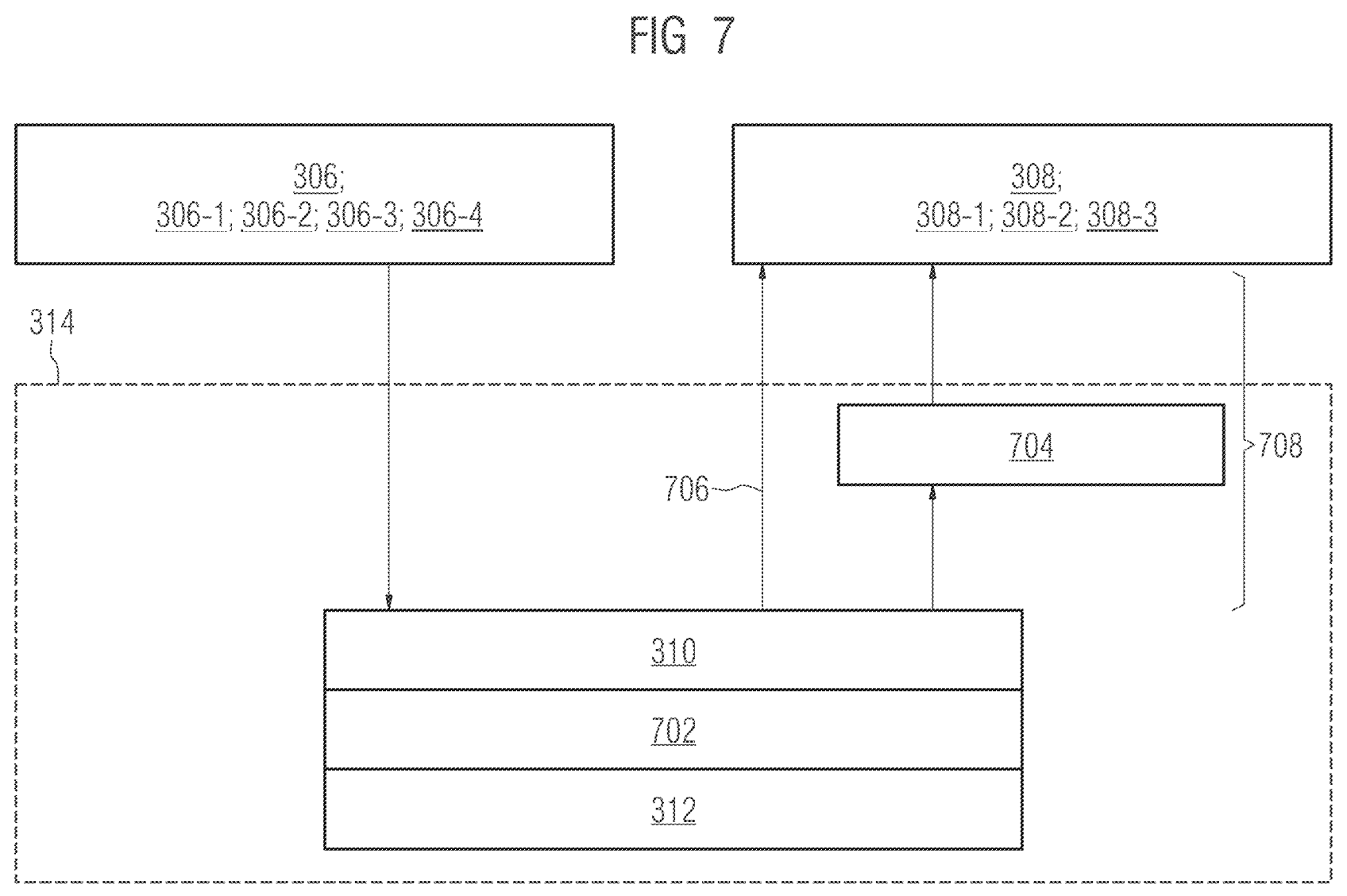

FIG. 7 schematically illustrates a second realization of joint training for the semantic image understanding algorithm 310 and the textual clinical concept algorithm 312 comprised in the clinical-concept-to-medical-image linking algorithm 314. In the example of FIG. 7, a further network 702 (also denoted as AI-powered orchestrator) is arranged in the middle (e.g., in terms of a data connection) between the semantic image understanding algorithm (and/or SIU) 310 and the textual clinical concept algorithm (and/or LLM) 312.

FIG. 7 shows two possible variations of a data flow for outputting the indication of the clinical workflow guidance in relation to the at least one second medical imaging data set.

At reference sign 706, a direct output is provided by the combination of the semantic image understanding algorithm 310 and the textual clinical concept algorithm 312 connected through the further network 702.

At reference sign, 708, and indirect output is schematically illustrated, in which the textual clinical concept algorithm (and/or LLM) 312 output passes through a still further network 704 (also denoted as AI-powered output classifier). An objective of the indirect output 708 is to achieve the highest possible performance for the given context 306-1 and provide safeguard and/or guard rails in case the output of the textual clinical concept algorithm (and/or LLM) 312 is too variable, and/or the textual clinical concept algorithm (and/or LLM) 312 misunderstands the context, e.g., confusing context of the AV with MV, and/or pulmonary valve.

The input of a workflow cycle for any one of the schematic examples in FIG. 6 and FIG. 7 may change with every workflow step taken by the user, e.g., as indicated at reference sign 306-4.

Wherever not already described explicitly, individual embodiments, or their individual aspects and features, described in relation to the drawings can be combined or exchanged with one another without limiting or widening the scope of the described invention, whenever such a combination or exchange is meaningful and in the sense of this invention. Advantages which are described with respect to a particular embodiment of present invention or with respect to a particular figure are, wherever applicable, also advantages of other embodiments of the present invention.

LIST OF CITED DOCUMENTS

[1] "Vision-Language Models for Vision Tasks: A Survey" by Jingyi Zhang et al., arXiv: 2304.00685v1 [cs.CV]
[2] "Recommendations for Cardiac Chamber Quantification by Echocardiography in Adults: An Update from the American Society of Echocardiography and the European Association of Cardiovascular Imaging" by Roberto M. Lang et al., Journal of the American Society of Echocardiography (onlinejase.com), http://dx.doi.org/10.1016/j.echo.2014.10.003
[3] "Guidelines for Performing a Comprehensive Transthoracic Echocardiographic Examination in Adults: Recommendations from the American Society of Echocardiography" by Carol Mitchell et al., Journal of the American Society of Echocardiography (onlinejase.com), https://doi.org/10.1016/j.echo.2018.06.004

LIST OF REFERENCE SIGNS

100 Method for multi-modality medical image clinical workflow guidance
S102 Step of receiving a user input
S104 Optional step of accessing a storage
S106 Step of assessing the received user input
S108 Step of outputting an indication of a clinical workflow guidance
200 Computing device
202 $1^{st}$ interface
204 Optional $3^{rd}$ interface
206 Assessment unit
208 $2^{nd}$ interface
210 Input-output interface
212 Processor
214 Memory
302 (in particular cardiovascular) medical imaging and information system
304-A $1^{st}$ medical imaging modality
304-B $2^{nd}$ medical imaging modality
306 Review of $1^{st}$ medical image data set
306-1 Clinical context
306-2 $1^{st}$ medical image data set
306-2A Cardiac CT focused on aortic valve, sagittal view
306-2B Cardiac CT focused on aortic valve, coronal view
306-2C Cardiac CT focused on aortic valve, axial view
306-2D Cardiac CT focused on aortic valve, VRT view
306-3 Measurement
306-4 User input

308 Selection of $2^{nd}$ medical image data set
308-1 $2^{nd}$ medical image data set (in particular its selection)
308-1A 2D TTE Parasternal short axis view, aortic valve
308-1B 2D TTE Parasternal long axis view, left ventricle
308-1C 2D TTE Parasternal long axis view, zoomed aortic valve
308-1D 2D TTE Apical 3 chamber view
308-1E 2D TTE Apical 3 chamber view with contrast
308-1F 2D TTE Doppler, aortic valve
308-1G 2D TTE Apical 4 chamber view
308-1H 2D TTE Apical 2 chamber view
308-2 Cardiac anatomy alignment
308-3 Next workflow step
310 Semantic image understanding algorithm
312 Textual clinical concept algorithm
314 Clinical-concept-to-medical-image linking algorithm
316 Clinical guidelines
602 One or more prompts
604 One or more queries
702 AI-powered joint orchestrator
704 AI-powered output classifier
706 Direct output
708 Indirect output

The invention claimed is:

1. A computer-implemented method for multi-modality medical image clinical workflow guidance, the method comprising:
receiving a user input in relation to a first medical image data set acquired by a first medical imaging modality, the first medical imaging modality comprising computed tomography, the user input comprising at least one of a medical measurement and a marked region of interest on the first medical image data set;
generating, by a semantic image understanding algorithm, extended metadata for the first medical image data set and at least one second medical image data set acquired by transthoracic echocardiography, the extended metadata comprising at least a cardiac phase identification and an image quality assessment score;
assessing, by a clinical-concept-to-medical-image linking algorithm, the received user input by mapping the user input to a clinical concept within a textual clinical concept algorithm using the extended metadata, wherein the clinical-concept-to-medical-image linking algorithm comprises the textual clinical concept algorithm and the semantic image understanding algorithm connected by iterative cycles of prompts and queries; and
outputting an indication of a clinical workflow guidance in relation to the at least one second medical image data set, wherein the indication comprises an automatic anatomy alignment of the first medical image data set and the at least one second medical image data set for side-by-side display on a user interface based on the clinical concept and the extended metadata.

2. The computer-implemented method according to claim 1, wherein the first medical image data set and/or the at least one second medical image data set comprises a two-dimensional and/or a three-dimensional image data set.

3. The computer-implemented method according to claim 1, wherein the multi-modality medical imaging comprises cardiac and/or cardiovascular imaging.

4. The computer-implemented method according to claim 1, wherein the semantic image understanding algorithm generates metadata in relation to the first medical image data set and/or the at least one second medical image data set, wherein the metadata are indicative of at least one of:

a view classification;

one or more anatomical landmarks and/or anatomical structures;

a zoom level;

a cardiac phase identification;

a contrast enhancement;

an image quality assessment; and/or a score for use cases.

5. The computer-implemented method according to claim 4, wherein the metadata are indicative of the score for use cases, and wherein the score is based on an image quality assessment at a predetermined phase within the cardiac cycle and/or anatomical structures comprised in the corresponding medical image data set.

6. The computer-implemented method according to claim 1, wherein the clinical-concept-to-medical-image linking algorithm comprises at least one trained artificial intelligence model.

7. The computer-implemented method according to claim 6, wherein the at least one trained artificial intelligence model comprises two jointly trained artificial intelligence models.

8. The computer-implemented method according to claim 6, wherein the at least one trained AI model is trained based on training data comprising:

input training data, the input training data comprising medical image data sets from multiple medical imaging modalities comprising the first medical imaging modality and the at least one second medical imaging modality, textual guidelines in relation to the clinical workflow, and functional couplings among anatomical structures and/or anatomical views in the medical image data sets; and output training data, the output training data comprising results of user interactions in relation to the input medical image data sets.

9. The computer-implemented method according to claim 1, wherein the user input is received by a user interface.

10. The computer-implemented method according to claim 1, further comprising:

accessing a storage for retrieving the at least one second medical image data set from a medical information system comprising at least one database for imaging and clinical data.

11. A system for multi-modality medical image clinical workflow guidance, the system comprising:

a first interface configured for receiving a user input in relation to a first medical image data set acquired by a first medical imaging modality, the first medical imaging modality comprising computed tomography, the user input comprising at least one of a medical measurement and a marked region of interest on the first medical image data set;

a processor configured to generate using a semantic image understanding algorithm, extended metadata for the first medical image data set and at least one second medical image data set acquired by transthoracic echocardiography, the extended metadata comprising at least a cardiac phase identification and an image quality assessment score, the processor further configured to assess using a clinical-concept-to-medical-image linking algorithm the received user input by mapping the user input to a clinical concept within a textual clinical concept algorithm using the extended metadata, wherein the clinical-concept-to-medical-image linking algorithm comprises the textual clinical concept algorithm and the semantic image understanding algorithm connected by iterative cycles of prompts and queries; and a second interface configured to output an indication of a clinical workflow guidance in relation to the at least one second medical image data set, wherein the indication comprises an automatic anatomy alignment of the first medical image data set and the at least one second medical image data set for side-by-side display on a user interface based on the clinical concept and the extended metadata.

12. The system according to claim 11, further comprising:

a memory configured for storing the at least one second medical image data set, wherein the storage is accessible for retrieval of the at least one second medical image data set from a medical information system comprising at least one database for imaging and clinical data; and a user interface configured to forward one or more user inputs to the first interface and to output one or more indications, received from the second interface, to the user.

13. The system according to claim 12, further comprising a third interface configured to access the memory.

14. A non-transitory computer-readable medium on which instructions are stored that can be read and executed by a computer for multi-modality medical image clinical workflow guidance, the instructions being to:

receive a user input in relation to a first medical image data set acquired by a first medical imaging modality, the first medical imaging modality comprising computed tomography, the user input comprising at least one of a medical measurement and a marked region of interest on the first medical image data set;

generate, by a semantic image understanding algorithm, extended metadata for the first medical image data set and at least one second medical image data set acquired by transthoracic echocardiography, the extended metadata comprising at least a cardiac phase identification and an image quality assessment score;

assess, by a clinical-concept-to-medical-image linking algorithm, the received user input by mapping the user input to a clinical concept within a textual clinical concept algorithm using the extended metadata, wherein the clinical-concept-to-medical-image linking algorithm comprises the textual clinical concept algorithm and the semantic image understanding algorithm connected by iterative cycles of prompts and queries; and output an indication of a clinical workflow guidance in relation to the at least one second medical image data set, wherein the indication comprises an automatic anatomy alignment of the first medical image data set and the at least one second medical image data set for side-by-side display on a user interface based on the clinical concept and the extended metadata.

* * * * *